(12) United States Patent
Gifford et al.

(10) Patent No.: US 11,266,989 B2
(45) Date of Patent: Mar. 8, 2022

(54) IMMUNODETECTION AND SEPARATION ON NANODLD

(71) Applicant: INTERNATIONAL BUSINESS MACHINES CORPORATION, Armonk, NY (US)

(72) Inventors: Stacey Gifford, Ridgefield, CT (US); Sung-Cheol Kim, New York, NY (US); Joshua T. Smith, Croton on Hudson, NY (US); Benjamin Hardy Wunsch, Mount Kisco, NY (US)

(73) Assignee: International Business Machines Corporation, Armonk, NY (US)

( * ) Notice: Subject to any disclaimer, the term of this patent is extended or adjusted under 35 U.S.C. 154(b) by 252 days.

(21) Appl. No.: 16/534,240

(22) Filed: Aug. 7, 2019

(65) Prior Publication Data

US 2021/0039101 A1   Feb. 11, 2021

(51) Int. Cl.
*B01D 15/34* (2006.01)
*B01L 3/00* (2006.01)
(Continued)

(52) U.S. Cl.
CPC ........ *B01L 3/502761* (2013.01); *B01D 15/34* (2013.01); *B01L 3/50273* (2013.01);
(Continued)

(58) Field of Classification Search
CPC ............ B01L 3/502761; B01L 3/5027; B01L 3/502753; B01L 2200/0652;
(Continued)

(56) References Cited

U.S. PATENT DOCUMENTS 8,883,691 B2   11/2014   True
8,999,731 B2    4/2015   Seul et al.
(Continued)

FOREIGN PATENT DOCUMENTS

WO   2017035262 A1   3/2017

OTHER PUBLICATIONS

Wunsch et al., "Nanoscale lateral displacement arrays for the separation of exosomes and colloids down to 20nm", Letters, Nature Nanotechnology, vol. 11, Nov. 2016, pp. 936-942.
(Continued)

*Primary Examiner* — Brian J. Sines
(74) *Attorney, Agent, or Firm* — L. Jeffrey Kelly

(57) ABSTRACT

An apparatus is provided. The apparatus may comprise a layer of a microfluidic chip. The layer may comprise a nanoscale deterministic lateral displacement (nanoDLD) array. The nanoDLD array may comprise a plurality of pillars arranged in a plurality of columns. Further, the nanoDLD array may separate particles from a purified fluidic sample associated with a bodily materials of an organism.

A method for purifying at least one target particle from a sample by utilizing a sized-based separation is provided. The method may include detecting the at least one target particle associated with the sample, by utilizing at least one detector molecule in a nanoDLD array. The method may then include separating the detected at least one target particle and the at least one detector molecule from a bump fraction in the sample based on a size of the detected at least one target particle.

16 Claims, 6 Drawing Sheets

(51) Int. Cl.
*G01N 33/53* (2006.01)
*G01N 30/00* (2006.01)

(52) U.S. Cl.
CPC ... *B01L 3/502707* (2013.01); *B01L 3/502715* (2013.01); *G01N 30/0005* (2013.01); *G01N 33/5304* (2013.01); *G01N 33/5308* (2013.01); *B01L 2200/0652* (2013.01); *B01L 2200/0668* (2013.01); *B01L 2400/086* (2013.01)

(58) Field of Classification Search
CPC ... B01L 2400/086; B01L 3/502; B01D 15/34; G01N 30/0005
See application file for complete search history.

(56) References Cited

U.S. PATENT DOCUMENTS

| | | | |
|---|---|---|---|
| 9,559,240 B1 | 1/2017 | Astier et al. | |
| 9,700,891 B2 | 7/2017 | Smith et al. | |
| 9,812,605 B2 | 11/2017 | Astier et al. | |
| 10,058,895 B2 | 8/2018 | Astier et al. | |
| 10,156,568 B2 | 12/2018 | Astier et al. | |
| 2015/0301058 A1 | 10/2015 | Scettini et al. | |
| 2015/0362413 A1* | 12/2015 | Zhang | B01L 3/502761 210/801 |
| 2016/0320389 A1 | 11/2016 | Astier et al. | |
| 2018/0080857 A1 | 3/2018 | Gifford et al. | |
| 2019/0224677 A1* | 7/2019 | Smith | G01N 1/4077 |
| 2020/0122143 A1* | 4/2020 | Smith | B01L 3/502746 |

OTHER PUBLICATIONS

Huang et al., "Continuous Particle Separation Through Deterministic Lateral Displacement", Science, vol. 304, May 14, 20104, pp. 987-990.

Inglis et al., "Critical particle size for fractionation by deterministic lateral displacement", The Royal Society of Chemistry, Lab Chip, vol. 6, Mar. 17, 2006, pp. 655-658.

* cited by examiner

IMMUNODETECTION AND SEPARATION ON NANODLD

BACKGROUND

The present invention relates generally to immunoassay and immunoseparation technology, and more specifically the use of microfluidic chips to facilitate target particle detection and separation based on size.

Regardless of the type of testing applied to a sample, the goal may be to detect or separate a particular analyte or biomarker that provides information about the sample. A key class of analyte tests may include immunoassays. For example, a common pregnancy test may detect the levels of the protein hormone human chorionic gonadotropin (hCG) in urine. Pregnancy tests may utilize antibodies, or immunoglobulins, that specifically recognize the analyte, hCG, and may react with a reagent to product a blue or pink line to represent the presence or absence of hCG in the urine sample.

Antibody-based detection methods may be considered the core of many biochemical assays in both clinical diagnostics and research applications. Antibodies may be produced by B lymphocytes (B-cells) as part of an immune response to a foreign antigen. The adaptive immune response, which is binding and neutralizing antigens (e.g., viruses) may be produced in most vertebrates. The utility of antibodies may be derived from the ability of the antibodies to recognize extremely specific epitopes, as small as a few atoms (e.g., a methylation site, —CH3) as well as the ability to produce antibodies to nearly any antigen, naturally-occurring or synthetic. Over the past decades, research has enabled large-scale production of natively-derived and synthetic antibodies. Indeed, there may be hundreds of thousands of antibodies commercially available for use in research and diagnostics.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to a more detailed description that is presented later. In one or more embodiments described herein, systems, apparatuses, and/or methods that may regard microfluidic chips, may facilitate the immunodetection and separation of one or more target particle by utilizing a nanoscale deterministic lateral displacement (nanoDLD) array.

According to an embodiment, an apparatus is provided. The apparatus may comprise a layer of a microfluidic chip. The layer may comprise a nanoscale deterministic lateral displacement (nanoDLD) array. The nanoDLD array may comprise a plurality of pillars arranged in a plurality of columns. Further, the nanoscale deterministic lateral displacement array may separate particles from a purified fluidic sample associated with a bodily materials of an organism.

According to an embodiment, a method for purifying at least one target particle from a sample by utilizing a sized-based separation is provided. The method may include detecting the at least one target particle associated with the sample, by utilizing at least one detector molecule in a nanoscale deterministic lateral displacement (nanoDLD) array. The method may then include separating the detected at least one target particle and the at least one detector molecule from a bump fraction in the sample based on a size of the detected at least one target particle.

Thus, various embodiments described herein may regard microfluidic chip designs and methods for achieving rapid target particle detection and separation at high throughput volumes. Further, high-throughput capabilities may be achieved via a nanoscale deterministic lateral displacement (nanoDLD) array. Therefore, one or more embodiments described herein may achieve target particle detection and separation based on size that may provide: high sensitivity, high volume throughput, continuous flow target particle purification and/or collection, reduced processing time, and/or compact architecture that may enable automation.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
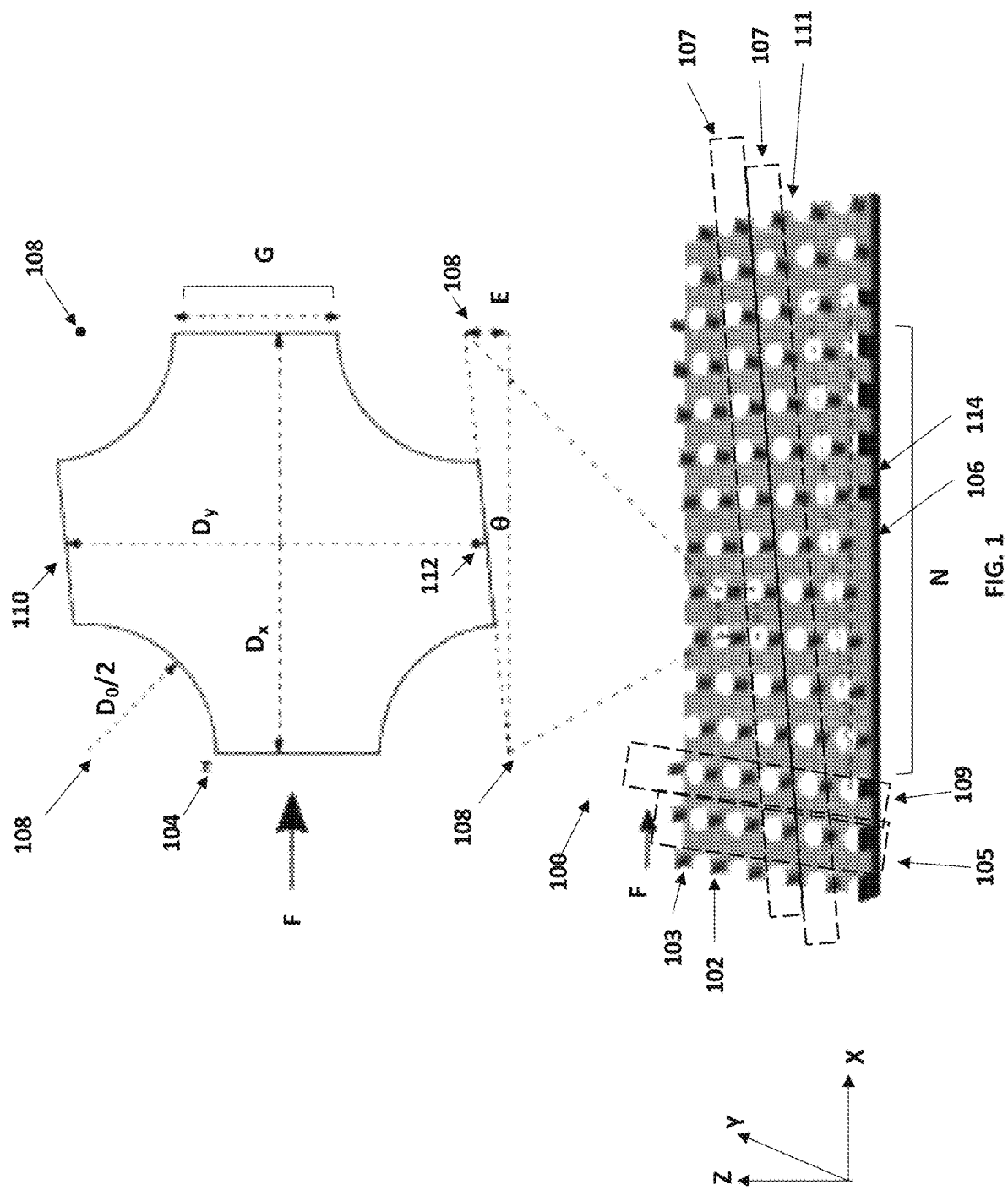
FIG. 1 illustrates a diagram of an example, non-limiting nanoscale deterministic lateral displacement (nanoDLD) array that may include a microfluidic chip in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments may be practiced without these specific details.

The following described exemplary embodiments provide a system and method for purifying at least one target particle from a sample by utilizing a sized-based separation. As such, the present embodiment has the capacity to improve the technical field of immunoassay and immunoseparation technology by transferring a surface marker specificity into a size-based separation by utilizing a nanoscale deterministic lateral displacement (nanoDLD) array on a microfluidic chip. More specifically, detecting and separating the target particle in a given sample in a liquid solution by utilizing a detector molecule in the nanoDLD array.

As previously described, regardless of the type of testing applied to a sample, the goal may be to detect or separate a particular analyte or biomarker that provides information about the sample. A key class of analyte tests may include immunoassays. For example, a common pregnancy test may detect the levels of the protein hormone human chorionic gonadotropin (hCG) in urine. Pregnancy tests may utilize antibodies, or immunoglobulins, that specifically recognize the analyte, hCG, and may react with a reagent to produce a blue or pink line to represent the presence or absence of hCG in the urine sample.

Antibody-based detection methods may be considered the core of many biochemical assays in both clinical diagnostics and research applications. Antibodies may be produced by B lymphocytes (B-cells) as part of an immune response to a foreign antigen. The adaptive immune response, which is binding and neutralizing antigens (e.g., viruses) may be produced in most vertebrates. The utility of antibodies may be derived from the ability of the antibodies to recognize extremely specific epitopes, as small as a few atoms (e.g., a methylation site, —CH3) as well as the ability to produce antibodies to nearly any antigen, naturally-occurring or synthetic. Over past decades, research has enabled large-scale production of natively-derived and synthetic antibodies. Indeed, there may be hundreds of thousands of antibodies commercially available for use in research and diagnostics.

Existing technologies that utilize antibody-based detection and separation methods may include Western blotting, immunoprecipitation (IP), enzyme-linked immunosorbent assays (ELISAs), surface plasmon resonance (SPR), and immunofluorescence imaging. While many of these assays, in particular ELISA and SPR, may be quite sensitive, detecting analyte levels as low as 10-15 mol (1 fmol). ELISA and SPR may rely solely on bulk assays and bulk signal and may not provide any single particle information, which may be relevant for situations where detection of a particular analyte in the context of the environment. For example, exosomes are small vesicles secreted by cells, which carry proteins on the surface and internal cargo. Using an antibody-based approach with existing methods may only provide information on the presence of a particular protein marker within a population of exosomes. There may be difficulties in determining whether a subpopulation of exosomes with particular characteristics carry a specific marker that may be relevant to function of the particular protein marker. As such, a single particle antibody-based detection method may be utilized to determine the subpopulation of exosomes carry that specific marker.

Additional challenges with existing antibody-based technologies may include the greater success rates for large samples volumes. For example, immunoprecipitation studies may include milliliters of sample and, as a result, may consume a large volume of antibodies that may be a cost-prohibitive reagent in many antibody-based methods. Even sensitive assays (e.g., ELISAs), frequently may include milliliter volumes of sample. Finally, in the case of immunoprecipitation, a tool for isolating a particular analyte from a sample, such as a batch process, may relies on Western blotting to determine if successful.

Therefore, it may be advantageous to, among other things, implement a high-sensitivity, single-particle method to detect and separate target particles on a microfluidic chip by utilizing a nanoscale deterministic lateral displacement (nanoDLD) to perform size-based separation of particles in a liquid sample to separate particles as small as 20 nanometers.

FIG. 1 illustrates a diagram of a non-limiting example of single nanoscale deterministic lateral displacement (nanoDLD) array that may be included on a microfluidic chip in accordance with one or more embodiments described herein. The nanoDLD array 100 may be located within a microchannel 103 and may include a plurality of pillars 102. The nanoDLD array 100 may operate on a principle of hydrodynamic chaos facilitated by one or more lattice structures 104 defined by the plurality of pillars 102. For example, the nanoDLD array 100 may have one or more geometries on the nanoscale. In the present embodiment, the nanoDLD array 100 may include a single fractionation bank. In one or more other embodiments, the nanoDLD array 100 may include two or more fractionation banks, which may be utilized to further purify the sample into the target particles.

The layer may include an inlet that can receive fluid, an outlet that may output a purified version of the fluid, and a nanoDLD array coupled between and in fluid communication with the inlet and the outlet. The fluid may flow through the microchannel 103, and thereby the nanoDLD array 100, in a direction indicated by the arrow "F" in FIG. 1. When a fluid flow F is directed through the nanoDLD array 100, the plurality of pillars 102 may act to deflect the fluid itself, causing a minor lateral component to the fluid flow which does not average out over the length of the microchannel 103. A net lateral displacement of the fluid may laterally move one or more target particles (e.g., biocolloids) including the fluid, and thereby may affect a spatial displacement or "condensation" within the nanoDLD array 100. The nanoDLD array 100 may concentrate one or more target particles into a concentrated stream. Further, the concentrated stream may include one or more target particles of a particular size and/or one or more target particles of various sizes.

Condensing one or more target particles of the fluid into a concentrated stream may be useful for concentrating a sample and/or preparing a sample for further separation into streams based on size/chemistry for purification. Since the nanoDLD array 100 may manipulate the fluid flow itself, target particles within the fluid, regardless of size, may experience the same lateral displacement.

In at least one embodiment, the lateral fluid displacement, by the nanoDLD array 100, may depend on the geometry of the one or more lattice structures 104 and/or the plurality of pillars 102.

As shown in FIG. 1, the plurality of pillars 102 may be arranged in a plurality of columns (e.g., column 105 traversing the microchannel 103 along the "y" axis) and/or a plurality of rows (e.g., rows 107, 111 traversing the microchannel 103 along the "x" axis). Additionally, adjacent columns (e.g., adjacent columns 105, 109) including the plurality of pillars 102 may be arranged offset each other (e.g., along the y axis), thereby positioning the plurality of rows at an angle to one or more walls 106 of the microchannel 103. FIG. 1 shows an expanded view of an exemplary lattice structure 104 defined by four pillars (e.g., pillar 102 may be an example of one of the four pillars).

The lattice structure 104 may be defined by four pillars of the plurality of pillars (e.g., where one or more pillars may be as shown at pillar 102). The lattice structure 104 may be located throughout the nanoDLD array 100 and/or at portion of the nanoDLD array 100. Further, the four pillars 102 may be adjacent to each other. For example, two adjacent pillars 102 of a column 105 and two adjacent pillars of the row 107 define a lattice structure 104 in which the column 105 and the row 107 may be adjacent to each other. FIG. 1 shows an example of four exemplary pillars, which may define a lattice structure 104, with dashed lines. The dashed lines may delineate an expanded view of an exemplary lattice structure 104 defined by the four exemplary pillars 102. One of ordinary skill in the art will recognize, that the nanoDLD array 100 may include one or more lattice structures 104 in one or more locations within the microchannel 103 of the nanoDLD array 100 other than the location of the exemplary, expanded lattice structure 104 shown in FIG. 1.

"E" may represent a lateral shift between centers 108 of pillars 102 of sequential columns. The lateral shift (e.g., represented by E) between sequential columns of pillars 102 may be characterized by formula 1:

$$D_y/N$$

The lateral shift (e.g., represented by E) of the nanoDLD array 100 may be greater than or equal 0.01 and/or less than or equal to 0.3.

"$D_y$" may represent a first distance across the lattice structure 104 along the y axis of the nanoDLD array 100. $D_y$ may extend from a first boundary 110 of the lattice structure 104 to a second boundary 112 of the lattice structure 104. Further, the first boundary 110 may be defined by a first center line of a first row of pillars 102, and the second boundary 112 may be defined by a second center line of a second row of pillars 102. In at least one embodiment, the first row of pillars 102 and the second row of pillars 102 may be adjacent to each other. In some embodiments, $D_y$ may be greater than or equal to 1 μm and/or less than or equal to 100 μm.

"N" may represent a number of sequential columns necessary to overcome the lateral shift and place two columns in alignment. For example, for the nanoDLD array 100 shown in FIG. 1, N may equal 10 as indicated by the dashed triangle 114, which exemplifies the lateral shift.

"$D_x$" may represent a second distance across the lattice structure 104 along the x axis of the nanoDLD array 100. $D_x$ may extend from a third boundary of the lattice structure 104 to a fourth boundary of the lattice structure 104. Further, the third boundary may be defined by a third center line of a first column of pillars 102, and the fourth boundary may be defined by a fourth center line of a second column of pillars 102. In at least one embodiment, the first column of pillars 102 and the second column of pillars 102 may be adjacent to each other. Additionally, $D_y$ may be measured along a first direction (e.g., along the y axis of the nanoDLD array 100) that is orthogonal to a second direction (e.g., along the x axis of the nanoDLD array 100), along which the $D_x$ may be measured. In some embodiments, $D_x$ may be greater than or equal to 1 μm and less than or equal to 100 μm.

"$D_0$" may represent a diameter of the plurality of pillars 102 defining a subject lattice structure 104. The $D_0$ of the pillars 102 may be greater than or equal to 0.5 μm and/or less than or equal to 99.5 μm. Further, the plurality of pillars 102 may have a height greater than or equal to 1 μm and/or less than or equal to 100 μm.

"G" may represent a pillar gap between adjacent pillars 102 of the same column. The nanoDLD array 100 may have a G of greater than or equal to 0.5 micrometers (μm) and/or less than or equal to 100 μm.

"θ" may represent an angle respective of a wall 106 of the microchannel 103. The θ may be greater than 0 degrees and less than 90 degrees.

A lattice ratio of the lattice structure 104 may be characterized by formula 2:

$$D_x/D_y$$

The lattice ratio may be greater than 0.1 and/or less than or equal to 1.0 to facilitate operation of the nanoDLD array 100. Additionally, a geometry ratio of the nanoDLD array 100 may be characterized by formula 3:

$$D_0/D_y$$

The geometry ratio may be greater than 0.1 and less than or equal to 1.0 to facilitate operation of the nanoDLD array 100. Additionally, the nanoDLD array 100 may include greater than or equal 100 columns of pillars 102 to facilitate operation. For example, the nanoDLD array 100 may have an overall length (e.g., along the x axis) greater than or equal to 0.1 millimeters (mm) and less than or equal to 10 mm. An embodiment of the nanoDLD array 100 may include one or more of the geometries that may facilitate a nanoDLD array 100 structures and/or facilitate high throughput rates.

In various embodiments, the plurality of pillars 102 may have a variety of shapes that may facilitate the geometric dimensions (e.g., regarding the nanoDLD array 100 and/or the lattice structure 104). For example, pillar 102 shapes may include a circular shape, a triangular shape, a square shape, a U shape, a napiform shape, a pentagonal shape (e.g., an irregular pentagon), and/or other similar shapes. In at least one embodiment, the nanoDLD array 100 may include a plurality of lattice structures 104 in which the respective lattice structures 104 may have varying geometries depending on the location of the particular lattice structure 104 along the nanoDLD array 100.

Figure 2:
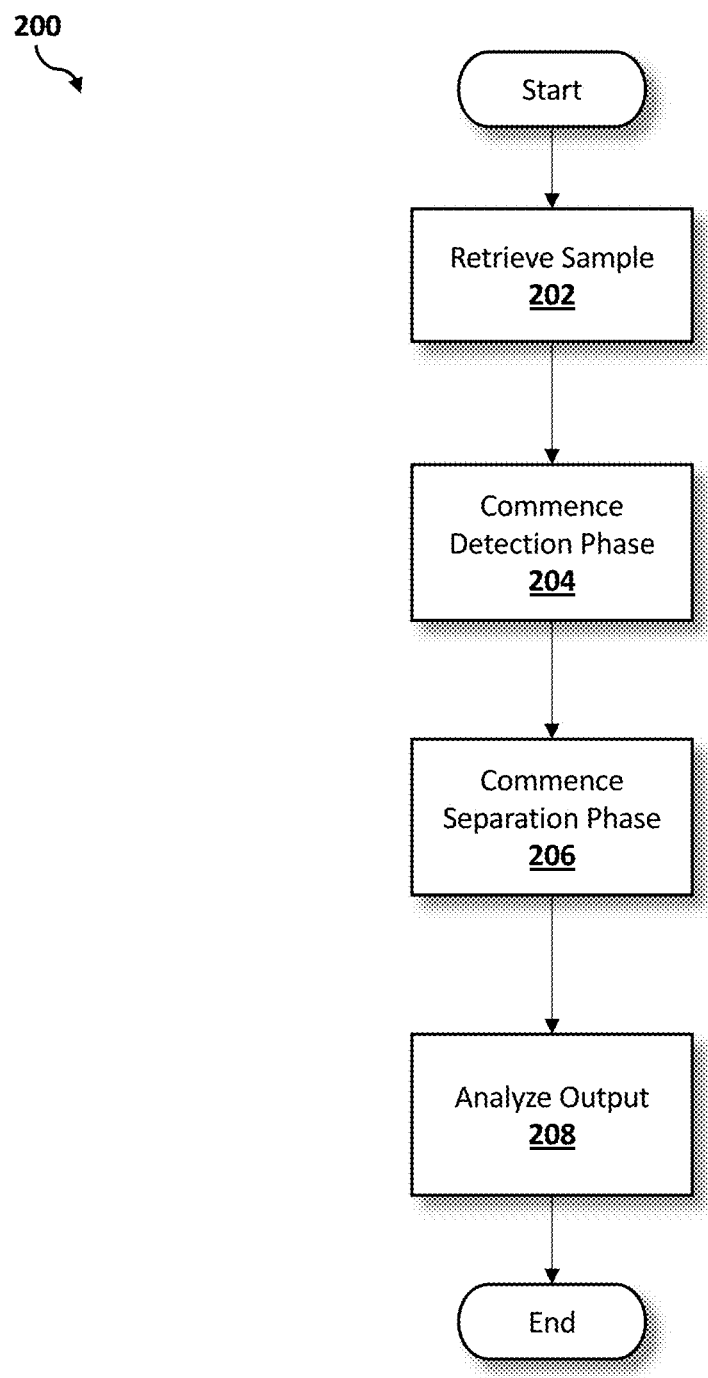
FIG. 2 illustrates a flow diagram of an example, non-limiting method that include immunodetection and separation of a target particle by utilizing nanoscale deterministic lateral displacement (nanoDLD) array in accordance with one or more embodiments described herein.

FIG. 2 illustrates a flow diagram 200 of an example, non-limiting method that include immunodetection and separation of a target particle by utilizing nanoscale deterministic lateral displacement (nanoDLD) on a microfluidic chip in accordance with one or more embodiments described herein.

According to at least one embodiment, the present method may utilize a nanoscale deterministic lateral displacement (nanoDLD) chip tool to translate surface marker-based detection and separation into a size-based approach thereby causing high-sensitivity, single-particle detection, low sample volume for detection and preparation, low reagent (antibody) consumption, and a continuous flow for detection and preparation.

According to at least one embodiment, the present method may utilize nanoDLD to separate particles as small as 20 nanometers (nm) based on size. For detection, the present embodiment may include one or more antibodies labeled with a fluorescent probe that may be employed to detect specific analytes in a given sample. Unbound antibodies may flow through the array unperturbed (i.e., zig-zag mode). In the presence of a specific analyte, antibodies may bind to the analyte, and binding between the antibody and analyte may increase the particle size and may cause the antibodies to commence a bumping mode. For smaller analytes, the present embodiment that may include two antibodies for the same analyte, but differing epitopes, may be coupled separately to beads. The bead-coupled antibodies may also flow through the array in zig-zag mode. In the presence of analyte, both antibodies may bind to their respective epitopes on the analyte. The combined side of the two antibody-coupled beads and analyte may cause the complex to commence a bumping mode. In both instances, this change in the angle of migration as detected by the fluorescence probe on the antibody in nanoDLD chip tool may indicate the presence of the analyte.

According to at least one embodiment, for separation of analytes, the present method may utilize a nanoDLD chip tool which may be used with gap sizes large enough that the antigen alone remains in zig-zag mode. Antibodies, which recognize the specific antigen, may be coupled to beads large enough to bump in the array. Antigens present in the sample may be bound to the antibody-coupled beads and may go into bump mode. Antibody-coupled beads and the bound antigen may be collected from the bump fraction only, and effectively purifying, separating or extracting the antigen away from the remaining sample.

At 202, a sample is retrieved. A sample (e.g., blood, serum, urine and other purified samples associated with the bodily materials of an organism) (i.e., biological sample) in a liquid (i.e., fluidic) solution may be transmitted from at least one source (e.g., patient samples, cell culture samples, plant samples, or other form of liquid/fluid-based samples) to at least one microfluidic chip or other form of storage medium. The transmission of the sample onto the chip may be driven by pressure (e.g., force from a pump or syringe that produces pressure). The microfluidic chip may include a nanoscale deterministic lateral displacement (nanoDLD) array on the microfluidic chip (i.e., nanoDLD array microfluidic device) that may then separate the particles of the sample into separate particles based on size on the nanoDLD microfluidic device or chip. As such, the nanoDLD array microfluidic device may function as a handheld device or a purification system.

In at least one embodiment, the sample may flow through the nanoDLD array at a rate greater than, to equal or about 1.0 nanoliters per hour as a throughout rate of the fluid.

For example, a blood sample is extracted from Patient Q, and then purified and labeled as Blood Sample Q131. The Blood Sample Q131 is then uploaded on storage medium in which the name and personal identifiers associated with Blood Sample Q131 is listed on the sample. The user then selects Blood Sample Q131, and the contents of Blood Sample Q131 is physically driven by a syringe into a nanoDLD chip tool mounted or affixed to the microfluidic chip.

Next, at 204, the detection phase is commenced. Utilizing a focuser (e.g., a hydrodynamic or a condenser focuser), the sample, which has been separated into smaller particles, may then be condensed into a single stream. The sample in the nanoscale deterministic lateral displacement (nanoDLD) array (i.e., nanoDLD chip tool) may be continuously monitored for fluorescence (e.g., fluorescent emission), as a tight focused beam. The user may have previously identify a specific target analytes (i.e., target particles) to detect and separate from the given sample.

Then, the detector molecule may be selected automatically by an external software program that may be activated by a user, or the detector molecule may be selected manually by the user. Either automatically or manually selected detector molecule (e.g., antibodies, nucleic acids and proteins) may be labeled with a fluorescent probe to detect specific target analytes (i.e., target particles) in the retrieved sample.

Prior to the commencement of the detection phase, the user may utilize an external software program to create a table or chart to category the detector molecules based on the target particle that the detector molecule may bound to. The table or chart may be generated based on data obtained from the user directly. Prior to finalizing the table or chart, the user may also review and verify the credibility and the reliability of the source that the data was extracted from.

The selection of the a detector molecule may be based on the interactions with target particle and a detector molecule (e.g., intrinsic or covalently coupled fluorescence). The primary criteria may be that fluorescently labeled detector molecule may be sufficiently small as to only zigzag in an unbound state and the target particle may be sufficiently large as to partially or fully bump for the fluorescent signal (e.g., an emission of electromagnetic radiation) to shift from the unbound zig-zag mode to the bound bump mode, when the detector molecule is bound to the target particle. The following Table 1 is an exemplary list of potential interactions between the detector molecules and the target particles that may be utilized to select a detector molecule based on the target particle:

TABLE 1

| Detector Molecule | Target Particle | Example |
| --- | --- | --- |
| Small molecule | Nucleic acid<br>Protein<br>Protein Complex<br>Ribosome<br>Exosome<br>Virus | YOYO-1 and DNA fragment |
| Antibody | Protein<br>Protein Complex<br>Ribosome<br>Exosome<br>Virus | Anti-CD81 antibody and exosomes |
| Nucleic Acid Oligomer | Complementary nucleic acid<br>Nucleic acid binding protein | Oligo probe and DNA |
| Protein/Binding Domain | Protein<br>Protein Complex<br>Nucleic acid<br>Exosome<br>Virus | SH2-domain and phosphorylated protein |

In at least one embodiment, the user may store the table or chart detailing the detector molecules with the corresponding target particles in a database associated with a user's computer or device.

An unbound detector molecule may flow through the nanoDLD array unperturbed (e.g., in a zig-zag mode). In the presence of a target particle, the detector molecule may bind to the target particle. Binding between the detector molecule (i.e., detector) and the target particle may increase the particle size and the detector molecule may be forced into a bumping mode (i.e., zig zag mode).

In at least one embodiment, for smaller target particles (e.g., as small as 20 nm), two detector molecules may be utilized for the same target particle. However, differing structures (e.g., binding sites or epitopes) may be coupled separately to detector molecules. Unbound, the detector molecules (e.g., bead-coupled antibodies) may flow through the nanoDLD array in zig-zag mode. In the presence of a target particle, both detector molecules may bind to their respective structures on the target particle. The combined side of the two detector molecules, and the target particle may force the detector-target particle complex (i.e., immunocomplex) into a bump mode.

Additionally, in any target particle size, a change in the angle of migration as detected by the fluorescence probe on the detector molecule in the nanoDLD array may indicate the presence of the target particle.

In at least one embodiment, the user may allocate a certain period of time for the detector molecule(s) to detect the target particle (e.g., default is 30 seconds). In some embodiments, if the user determines that the detector molecule(s) fails to detect the target particle in the given sample, then the user may then proceed to end the nanoDLD immunodetection and separation method for this retrieved sample and/or may proceed with a different sample.

Continuing with the previous sample, previously the user selected Virus TP-7. Since Protein XYZ has been identified in various medical journals as a good detector molecule for Virus TP-7, the user selects Protein XYZ as the detector molecule for Virus TP-7 in Blood Sample Q131. The unbound Protein XYZ, which was separated from the other particles in Blood Sample Q131, remains in the nanoDLD array. The user physically drives the Protein XYZ into the nanoDLD array, and within 15 seconds, Protein XYZ binds to Virus TP-7 and forces the Virus TP-7 and Protein XYZ combination into a zig-zag mode.

Then, at 206, the separation phase is commenced. During the separation phase, the user may utilize a detector molecule in the nanoDLD array may be utilized with gap sizes that are large enough for the target particle alone to remain in zig-zag mode (i.e., create a bump or forced into bump mode). Target particle present in the retrieved sample may be bound to the detector molecules and forced to create a bump in the nanoDLD array (i.e., bump mode). The target particle and detector molecules may be collected from the bump fraction only, effectively purifying the target particle away from the remaining sample.

Continuing with the previous sample, the Virus TP-7 and Protein XYZ combination creates a bump in the sample, thereby separating the Virus TP-7 from the rest of Blood Sample Q131.

Then, at 208, the output is analyzed. A fluorescent microscope may be utilized by the user to analyze the output (i.e., findings) or fluorescent signal(s) emitted from the nanoDLD array. In at least one embodiment, the output from the nanoDLD array may be captured as images utilizing an external imaging software program on the user's computer or device. The captured image may be further analyzed and stored in a database associated with the user's computer, device, or other form of storage medium selected by the user. As such, the images may be reviewed and analyzed at a later date.

Continuing the previous example, the user is then utilizes a fluorescent microscope to analyze the fluorescent signal emitted by the output of the nanoDLD array to determine that the Virus TP-7 has been successfully detected in Blood Sample Q131 and separated from Blood Sample Q131.

Figure 3:
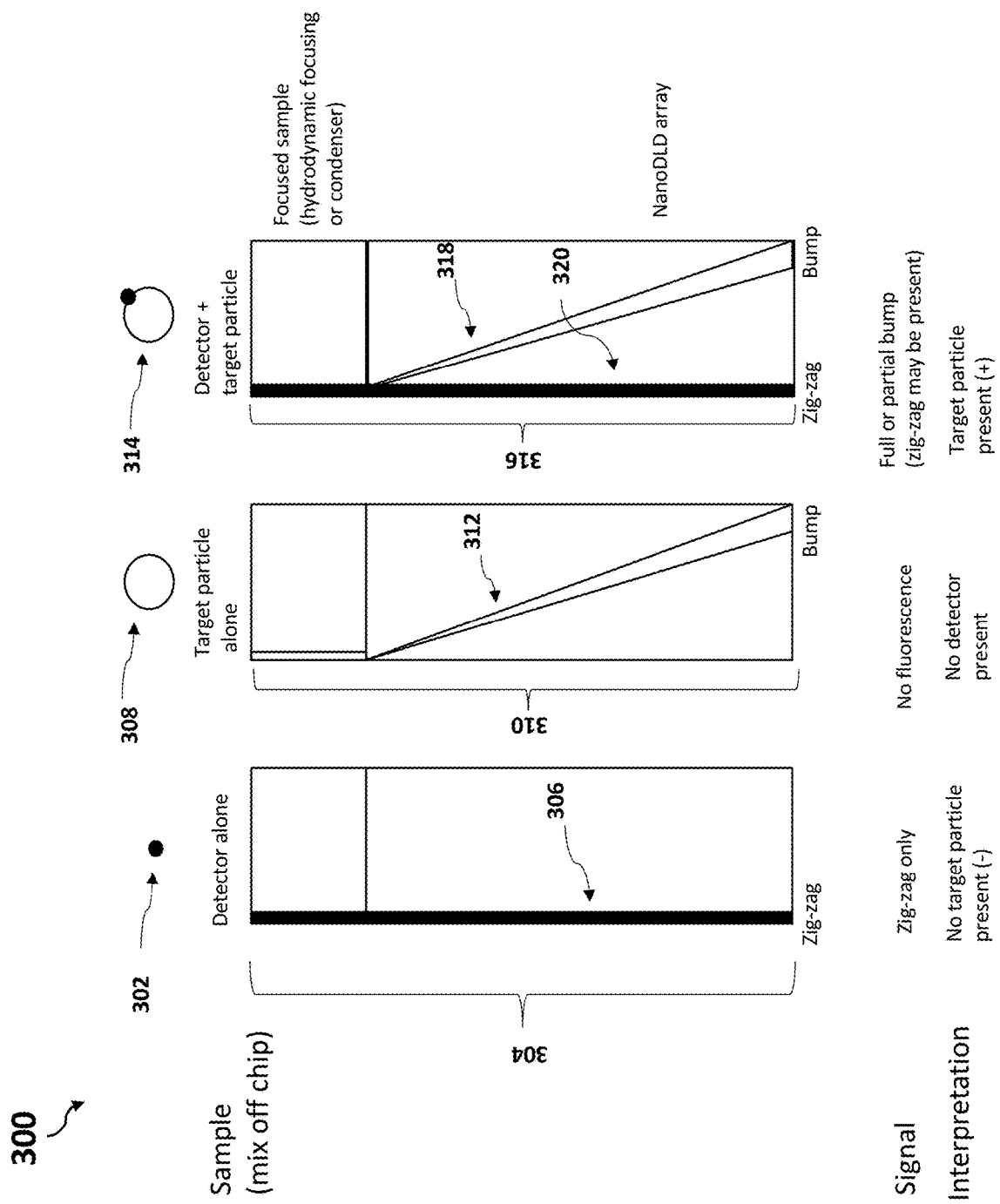
FIG. 3 illustrates a block diagram of an output from an example, non-limiting method depicted in FIG. 2 for target particles greater than 20 nanometers (nm) in accordance with one or more embodiments described herein.

FIG. 3 is a block diagram 300 illustrating the output of the exemplary method of immunodetection and separation depicted in FIG. 2 for target particles greater than 20 nanometers (nm) depicted in FIG. 2 in accordance with an illustrative embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

The size of a nanoDLD bump particle (i.e., target particle 308) may be as small at 20 nm. However, the target particle 308 above this cutoff include viruses, exosomes, ribosomes, DNA, and large protein complexes. The gap size of the nanoDLD array may be selected by the user for the target particle 308 to achieve the maximum bump angle 318 regardless of the size of the target particle.

In sample 304, the detector (i.e., detector molecule) alone 302 may present a zig zag signal 306 in the absence of a target particle. Therefore, the sample 304 may be interpreted as lacking a target particle (e.g., no target particle present).

In sample 310, the target particle alone 308 may present a bump 312 with no fluorescence signal. Therefore, the sample 310 may be interpreted as lacking a detector (e.g., no detector present).

However, in focused sample 316 that underwent hydrodynamic focusing or a condenser in a nanoDLD array, the combined detector and target particle 314, a full or partial bump 318 may be present, as well as a zig zag signal 320. Therefore, the sample 316 may be interpreted as including a target particle (e.g., target particle present).

Figure 4:
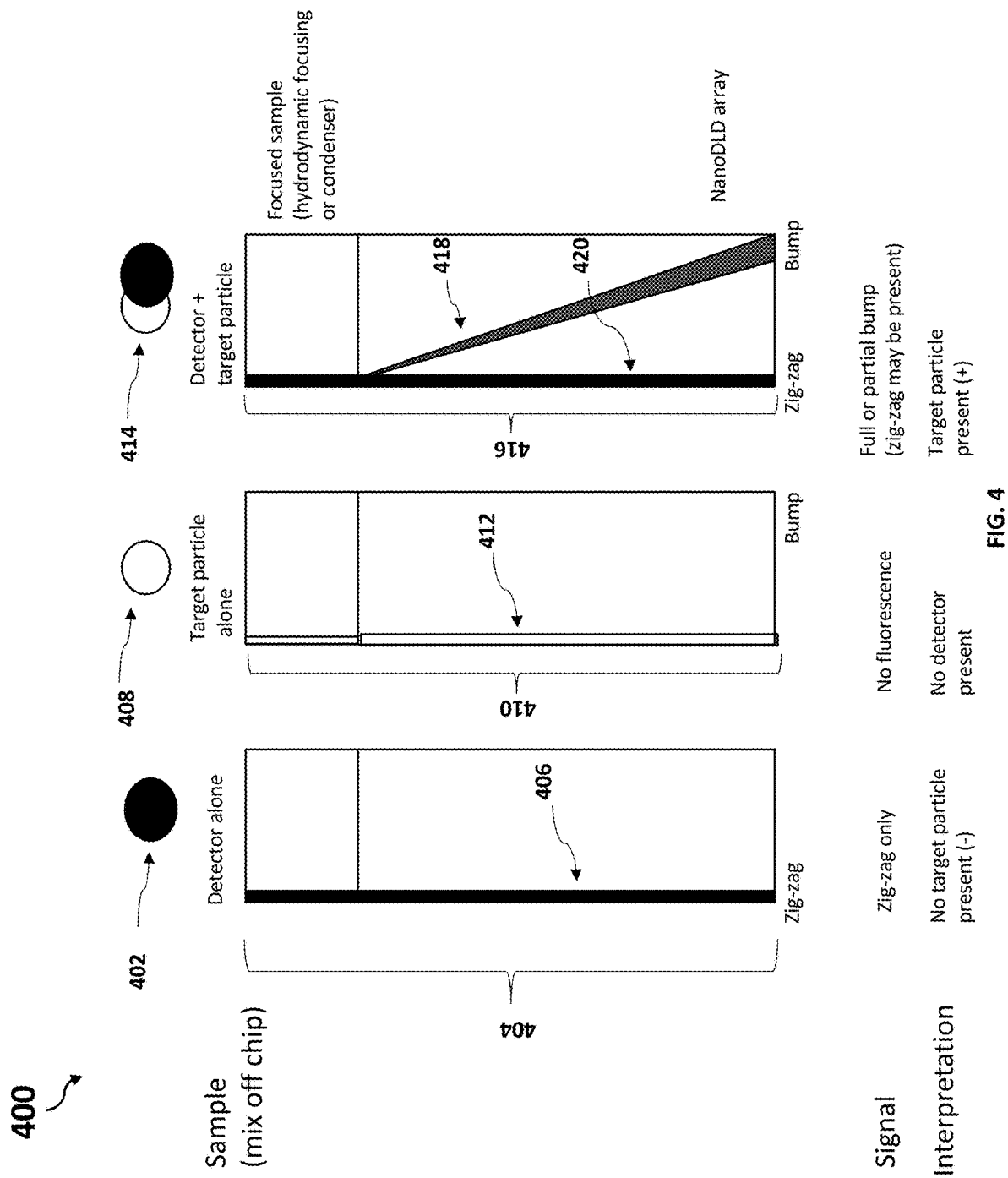
FIG. 4 is a block diagram of an output from an example, non-limiting method depicted in FIG. 2 for target particle complexes greater than 20 nanometers (nm) in accordance with one or more embodiments described herein.

FIG. 4 is a block diagram 400 illustrating the output of the exemplary method of immunodetection and separation depicted in FIG. 2 for target particle complexes greater than 20 nanometers (nm) depicted in FIG. 2 in accordance with an illustrative embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

In sample 404, the detector alone 402 may present a zig zag signal 406 in the absence of a target particle. Therefore, the sample 404 may be interpreted as lacking a target particle (e.g., no target particle present).

In sample 410, the target particle alone 408 may present a bump 412 with no fluorescence signal. Therefore, the sample 410 may be interpreted as lacking a detector (e.g., no detector present). In at least one embodiment, absent the detector (e.g. a target particle alone 408) may be invisible. The presence of the detector may cause the bump fraction to be seen.

However, in focused sample 416 that underwent hydrodynamic focusing or a condenser in a nanoDLD array, the combined detector and target particle 414 (i.e., target particle complex, or target particle coupled with detector), a full or partial bump 418 may be present, as well as a zig zag signal 420. Therefore, the sample 416 may be interpreted as including a target particle (e.g., target particle present).

Figure 5:
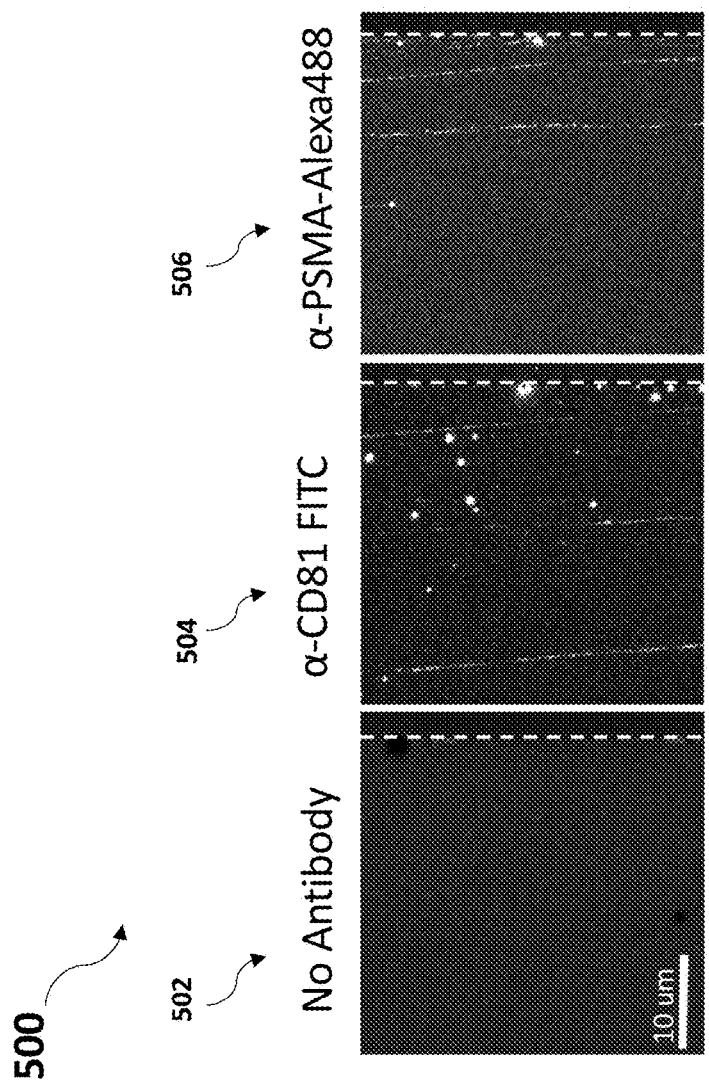
FIG. 5 is a block diagram of the particle detection comparison by fluorescence depicted in FIG. 2 in accordance with one or more embodiments described herein.

FIG. 5 is a block diagram 500 illustrating the comparison of the particle detection by fluorescence depicted in FIG. 2 in accordance with an illustrative embodiment of the present invention. It should be appreciated that FIG. 5 provides only an illustration of one implementation and does not imply any limitations with regard to the environments in which different embodiments may be implemented. Many modifications to the depicted environments may be made based on design and implementation requirements.

The two detector molecules (e.g., antibodies) may be used to detect exosomes carrying specific protein surface markers. In sample 502, there may be no antibody to detect the target particle, and therefore, there may be no fluorescence or signal expressed in sample 502. In sample 504, the first marker (e.g., CD-81), which may be detected with a CD-81 antibody coupled to FITC dye. In sample 506, the second marker (e.g., PSMA), which may be detected with a PSMA antibody coupled to Alexa488 dye. The exosomes alone may show no fluorescence, but in the presence of either detector molecule, clear partial and full-bump traces may be detected in the nanoDLD array.

Figure 6:
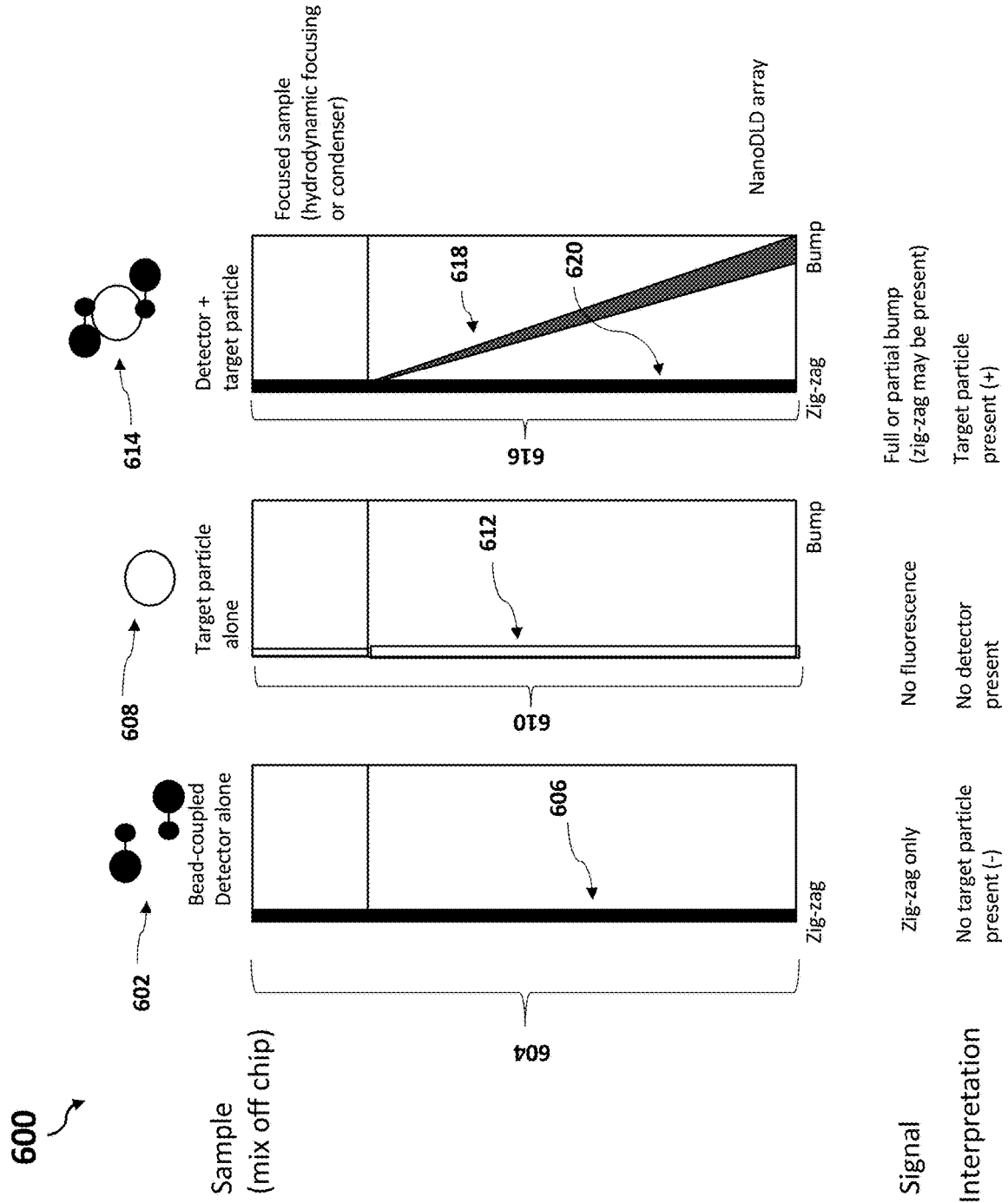
FIG. 6 is a block diagram of an output from an example, non-limiting method depicted in FIG. 2 for target particles smaller than 20 nanometers (nm) in accordance with one or more embodiments described herein.

FIG. 6 is a block diagram 600 illustrating the output of the exemplary method of immunodetection and separation depicted in FIG. 2 for target particles smaller than 20 nanometers (nm) or too small to enter bump mode when bound to a detector molecule depicted in FIG. 2 in accordance with an illustrative embodiment of the present invention. It should be appreciated that FIG. 6 provides only an illustration of one implementation and does not imply any limitations with regard to the environments in which different embodiments may be implemented. Many modifications to the depicted environments may be made based on design and implementation requirements.

For target particles that are smaller than 20 nm or too small in size to enter bump mode when bound to a detector molecule, two or more detector molecules may be utilized. Each detector molecule may recognize a different structure on the target particle (e.g., binding site, epitope, chemical modification, protein, nucleic acid sequence). Each detector molecule may be coupled to a fluorescent polystyrene bead. Each bead-bound detector molecule size may be arranged for the unbound state of the detector molecule to be below the critical concentration and travel through the array in a zig-zag mode. For example, in sample 604, the bead-coupled detector alone 602, in the absence of target particle, the two bead-bound detectors 602 may not interact and may not display fluorescence in a zig-zag signal 606. In sample 610, in the presence of the target particle alone 608, there may be no fluorescence or bump 612 in the absence of a detector. In sample 616, the two bead-bound detectors may bind to the target particle with different molecular specificity forming detector-target particle complexes 614. The combined size of the two beads may increase the total particle size for a sufficiently large complex to enter a partial or full bump mode 618. This transition of fluorescence signal from zig-zag 620 to partial or full bump mode 618 may serve as a positive signal for the presence of the target particle.

In at least one embodiment, the unbound fluorescent detector molecule and the unbound target particle may be observed in zig-zag mode. Upon binding, the detector-target particle complex (i.e., the combination of the detector molecule and the target particle) may be sufficiently large enough to enter partial or full bump mode. The binding event may trigger a shift in the fluorescence signal from zig-zag to bump indicating the presence of the target particle.

The present invention may utilize a nanoDLD chip tool to translate surface marker-based detection and separation into a size-based approach to enable sample isolation and preparation. In addition, any molecular interaction coupled with beads to trigger a sized-based separation of particles down to the size of small molecules less than 20 nm in diameter, in the absence or presence of immobilization. The present invention may further create a single-particle detection that increase sensitivity, may utilize a low sample volume for detection and preparation, and low reagent (antibody) consumption, and may provide a continuous flow for detection and preparation.

The present invention may improve the field of immunodetection and separation of target particles by utilizing a nanoDLD array on a microfluidic chip and the injection of detector molecules to detect the presence of a target particle, through the emission of a fluorescent signal, and further separate the target particles from the remaining sample, even if the target particle is less than 20 nanometers in size. Additionally, the present method and/or apparatus may increase ease and sensitivity in the point-of-care diagnostics by creating an approach to separation of target particles based on size in which target particles greater than 20 nanometers are separated differently than target particles that are smaller than 20 nanometers.

The present method and/or apparatus further includes the utility of the nanoDLD array microfluidic device that may separate particles by size as a detector of the formation of immunocomplexes (i.e., detector-target particle complexes). As target particles bind to the detector, which may be viewed by fluorescence or some other means of detection, the nanoDLD array may move the larger target particles into a specific bump stream from the smaller zigzag stream. Such a shift in target particles may result in a shift in the fluorescence signal, which enables detection of the formation of immunocomplexes, serving as a proxy for the presence of a specific analyte (i.e., target particle). In summary, this coupling of the nanoDLD with immunocomplexes may form a new and easily adaptable immunoassay.

It may be appreciated that FIGS. 2-6 provide only an illustration of one embodiment and do not imply any limitations with regard to how different embodiments may be implemented. Many modifications to the depicted embodiment(s) may be made based on design and implementation requirements.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

What has been described above include mere examples of systems, computer program products and computer-implemented methods. It is, of course, not possible to describe every conceivable combination of components, products and/or computer-implemented methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An apparatus, comprising:
a layer of a microfluidic chip, the layer comprising an inlet that receives fluid, an outlet that outputs a purified version of the fluid, and a nanoscale deterministic lateral displacement (nanoDLD) array coupled between and in fluid communication with the inlet and the outlet,
wherein the nanoDLD array comprises a plurality of pillars arranged in a plurality of columns,
wherein a pillar gap sized to facilitate a throughput rate of the fluid of greater than or equal to about 1.0 nanoliter per hour is located between a first pillar of the plurality of pillars in a first column of the plurality of columns and a second pillar of the plurality of pillars in the first column, and
wherein the plurality of pillars define a lattice, wherein a first ratio is less than or equal to a first defined value, the first ratio characterized by $D_x/D_1$, wherein $D_x$ represents a first distance across the lattice in a first direction, and wherein $D_y$ represents a second distance across the lattice in a second direction, and wherein the first direction is orthogonal to the second direction.

2. The apparatus of claim 1, wherein the microfluidic chip is a lab-on-chip designed to purify a biological sample,
wherein the biological sample is in a fluidic solution,
wherein the biological sample is purified.

3. The apparatus of claim 1, wherein the apparatus comprises at least one of a handheld device or a purification system.

4. The apparatus of claim 1, wherein the nanoDLD array separates at least one target particle from a purified biological sample.

5. The apparatus of claim 1, wherein the plurality of pillars define a lattice that laterally displaces the fluid flowing through the nanoDLD array.

6. The apparatus of claim 1, wherein the plurality of pillars facilitate one or more geometric dimensions.

7. The apparatus of claim 1, wherein the plurality of pillars comprises one or more shapes,
wherein the one or more shapes is selected from a group consisting of: a circular shape; a triangular shape; a square shape; a U shape; a napiform shape; and a pentagonal shape.

8. The apparatus of claim 1, wherein the nanoDLD array comprises one single fractionation bank.

9. An apparatus, comprising:
a layer of a microfluidic chip, the layer comprising an inlet that receives fluid, an outlet that outputs a purified version of the fluid, and a nanoscale deterministic lateral displacement (nanoDLD) array coupled between and in fluid communication with the inlet and the outlet,
wherein the nanoDLD array comprises a plurality of pillars arranged in a plurality of columns,
wherein a pillar gap sized to facilitate a throughput rate of the fluid of greater than or equal to about 1.0 nanoliter per hour is located between a first pillar of the plurality of pillars in a first column of the plurality of columns and a second pillar of the plurality of pillars in the first column,
wherein the plurality of pillars define a lattice, wherein a first ratio is less than or equal to a first defined value, the first ratio characterized by $D_x/D_y$, wherein $D_x$ represents a first distance across the lattice in a first direction, and wherein $D_y$ represents a second distance across the lattice in a second direction, and wherein the first direction is orthogonal to the second direction, and
wherein a second ratio is greater than a second defined value, the second ratio characterized by $D_0/D_y$, wherein Do represents a diameter of the plurality of pillars.

10. The apparatus of claim 9, wherein the microfluidic chip is a lab-on-chip designed to purify a biological sample,
wherein the biological sample is in a fluidic solution,
wherein the biological sample is purified.

11. The apparatus of claim 9, wherein the apparatus comprises at least one of a handheld device or a purification system.

12. The apparatus of claim 9, wherein the nanoDLD array separates at least one target particle from a purified biological sample.

13. The apparatus of claim 9, wherein the plurality of pillars define a lattice that laterally displaces the fluid flowing through the nanoDLD array.

14. The apparatus of claim 9, wherein the plurality of pillars facilitate one or more geometric dimensions.

15. The apparatus of claim 9, wherein the plurality of pillars comprises one or more shapes,
wherein the one or more shapes is selected from a group consisting of: a circular shape; a triangular shape; a square shape; a U shape; a napiform shape; and a pentagonal shape.

16. The apparatus of claim 9, wherein the nanoDLD array comprises one single fractionation bank.

* * * * *